United States Patent
Guzman Rabanillo et al.

(10) Patent No.: US 9,766,210 B2
(45) Date of Patent: Sep. 19, 2017

(54) METHOD FOR EVALUATING THE INSTALLATION OF BLIND RIVETS, METHOD AND SYSTEM FOR INSTALLING BLIND RIVETS, METHOD AND SYSTEM FOR OBTAINING A PATTERN, AND AIRCRAFT

(71) Applicant: Airbus Operations, S.L., Madrid (ES)

(72) Inventors: Desirée Guzman Rabanillo, Puerto Real (ES); Juan Ramón Astorga Ramírez, Puerto Real (ES); Javier Camacho De Miguel, San Sebastián (ES); Agustín Sáenz Fernandez, San Sebastián (ES); Maria Asunción Rivero Rastrero, San Sebastián (ES)

( * ) Notice: Subject to any disclaimer, the term of this patent is extended or adjusted under 35 U.S.C. 154(b) by 510 days.

(21) Appl. No.: 13/828,815

(22) Filed: Mar. 14, 2013

(65) Prior Publication Data

US 2013/0250730 A1    Sep. 26, 2013

(30) Foreign Application Priority Data

Mar. 23, 2012    (EP) .................................... 12382106

(51) Int. Cl.
*G01N 29/07* (2006.01)
*B21J 15/28* (2006.01)
*G01N 29/34* (2006.01)

(52) U.S. Cl.
CPC .............. *G01N 29/07* (2013.01); *B21J 15/28* (2013.01); *B21J 15/285* (2013.01); *G01N 29/348* (2013.01); *G01N 2291/2691* (2013.01)

(58) Field of Classification Search
CPC .......... B21J 15/28; B21J 15/285; G01N 29/38
See application file for complete search history.

(56) References Cited

U.S. PATENT DOCUMENTS 3,292,413  A  *  12/1966  Falcioni .................... B21J 15/24
                                                          29/525.06
4,201,093  A  *   5/1980  Logan ..................... G01N 29/07
                                                             73/609

(Continued)

FOREIGN PATENT DOCUMENTS

CN          1 638 888 A      7/2005
CN       102 083 567 A       6/2011

(Continued)

OTHER PUBLICATIONS

Chinese Search Report for Application No. 2013 100 953 05.0 dated Oct. 21, 2015.

(Continued)

*Primary Examiner* — R. A. Smith
*Assistant Examiner* — Herbert K Roberts
(74) *Attorney, Agent, or Firm* — Jenkins, Wilson, Taylor & Hunt, P.A.

(57) ABSTRACT

A method for evaluating installation of blind rivets including measuring the "cycle time" represented "$y_0$", transmitting sound waves through the blind rivet installed in the structure, measuring the "travel time" represented "$x_0$", relating "travel time" and "cycle time", and obtaining a pair of times $(x_0, y_0)$, providing a time relation pattern establishing a borderline between an area of suitable rivets and an area of unsuitable rivets, the border represented $y=f(x)$, so for cycle time values greater than $y=f(x)$, it is considered a "suitable area", for cycle time values less than $y=f(x)$, it is considered an "unsuitable area", representing pair $(x_0, y_0)$ in the graphic representation and verifying if the value of $y_0$ is greater or less than the value of $y=f(x0)$, classifying installation of the rivet as suitable or unsuitable according to the verification.

13 Claims, 5 Drawing Sheets

(56) References Cited

U.S. PATENT DOCUMENTS

| | | | | |
|---|---|---|---|---|
| 4,901,431 A * | 2/1990 | Gast | .................. | B21J 15/105 227/1 |
| 5,035,353 A * | 7/1991 | Smart | .................. | B21J 15/105 227/112 |
| 5,343,785 A * | 9/1994 | Holt | .................. | B23P 19/066 73/761 |
| 5,661,887 A * | 9/1997 | Byrne | .................. | B21J 15/105 227/2 |
| 5,666,710 A | 9/1997 | Weber et al. | | |
| 6,314,817 B1 * | 11/2001 | Lindback | .............. | B23P 19/066 73/761 |
| 7,024,746 B2 * | 4/2006 | Weeks | .................. | B21J 15/105 29/243.519 |
| 7,313,851 B2 | 1/2008 | Wang et al. | | |
| 7,536,764 B2 * | 5/2009 | Weeks | .................. | B21J 15/105 29/243.519 |
| 7,791,254 B1 * | 9/2010 | Gibson | .................. | G01H 11/08 310/336 |
| 2006/0230609 A1 * | 10/2006 | Wang | .................. | B21J 15/025 29/798 |
| 2007/0033788 A1 | 2/2007 | Chitty et al. | | |
| 2007/0113390 A1 * | 5/2007 | Chitty | .................. | B21J 15/043 29/243.523 |
| 2007/0175010 A1 | 8/2007 | Wang et al. | | |
| 2008/0209707 A1 | 9/2008 | Cioto et al. | | |
| 2009/0320271 A1 | 12/2009 | Perez Martin et al. | | |

FOREIGN PATENT DOCUMENTS

| | | | | |
|---|---|---|---|---|
| EP | 0 738 550 A2 | 10/1996 | | |
| EP | 0 739 664 | 11/1996 | | |
| GB | 2425179 | 10/2006 | | |
| GB | 2425179 A * | 10/2006 | ............ | B21J 15/285 |
| SE | WO 2006110089 A1 * | 10/2006 | ............ | B21J 15/285 |
| WO | WO 2006/110089 | 10/2006 | | |
| WO | WO 2007/028218 | 3/2007 | | |

OTHER PUBLICATIONS

Chinese Office Action for Application No. 2013 100 953 05.0 dated Oct. 30, 2015.

* cited by examiner

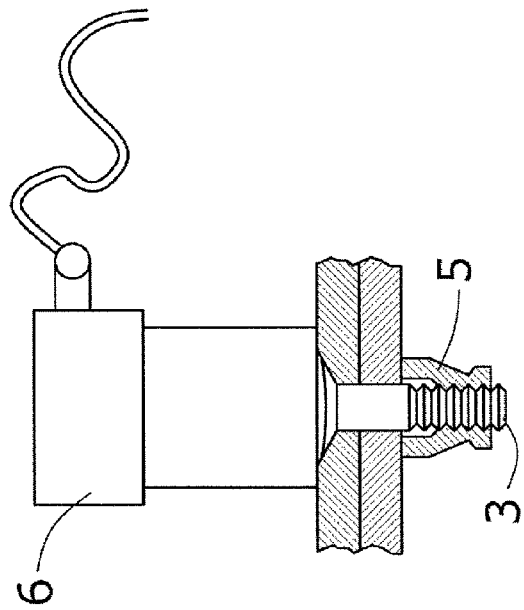
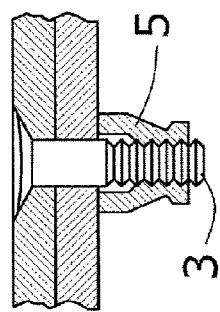
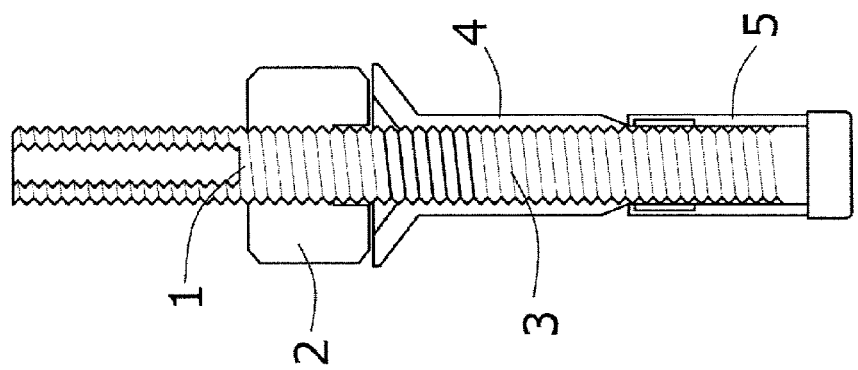

METHOD FOR EVALUATING THE INSTALLATION OF BLIND RIVETS, METHOD AND SYSTEM FOR INSTALLING BLIND RIVETS, METHOD AND SYSTEM FOR OBTAINING A PATTERN, AND AIRCRAFT

CROSS-REFERENCE TO RELATED APPLICATION

This application claims the benefit of the filing date of European Application Serial No. EP12382106.8 filed Mar. 23, 2012 the disclosure of which is hereby incorporated herein by reference.

TECHNICAL FIELD

The present invention relates to a method and system for evaluating the installation of blind rivets used in attaching structures, a system and method for generating a pattern relating installation "cycle time" and "travel time", and an aircraft comprising a structure installed with the systems described above.

BACKGROUND

Blind rivets are widely used in closed aeronautical structures, where attachments have very restricted access on one of the sides, with no possibility of accessing or even viewing the rear part of the attachment. Consequently, the rivet quality evaluation process is carried out exclusively from the access face ('exposed face').

Blind rivets are inserted in the corresponding holes, and the riveting process is carried out until the stem of the rivet breaks, the rivet being installed. However, since accessing the blind face (or unexposed face) is not possible, it is not possible to carry out a complete quality control of the attachment.

There is no absolute assurance that the inspection method supplied by rivet manufacturers detects faults inside the rivet or in its closing head (unexposed face) when the choice of rivet is not suitable according to the thickness of the attachment, reaching a critical situation when the thickness is close to the limit between two lengths of the rivet.

Although the process parameters leading to the correct installation of rivets are known in the vast majority of installations, and despite the current control methods, a significant number of attachments are still produced in which the rivets are incorrectly installed. Consequently, the attachments designed by means of blind rivets must be oversized, increasing the number of necessary rivets, manufacturing times, weight and cost of the resulting attachments. Furthermore, the existing methods based exclusively on monitoring the process do not contemplate errors due to machining steps after the riveting itself, such as machining the mandrel, a necessary operation in aeronautical applications for meeting the aerodynamics requirements.

A system which, in a non-destructive way, informs of the correct installation of rivets, it is necessary to assure the correct installation of the rivets with maximum assurance.

Until now methods for inspecting the state of the rivet have been proposed. Most of the proposed methods are based on monitoring the riveting process. These methods are based on measuring one or several signals during the riveting process and subsequent analysis thereof, either for comparing with standard curves or for extracting evaluation values which are subsequently compared with reference values. Some of the existing methods based on monitoring the process are listed below. First, document U.S. Pat. No. 5,666,710A describes monitoring the "force" and "displacement" signals and the evaluation value is the energy invested in the riveting process. In patent U.S. Pat. No. 7,313,851B2 the same signals are monitored but the evaluation value is an instant comparison with the standard curve characterising installation processes. Document WO2007028218A1 describes monitoring the torsion angle in the rivet.

These methods based exclusively on monitoring the process do not contemplate errors due to machining steps after the riveting itself, which steps are necessary in constructing riveted structures and can induce defects in the rivets.

Unlike methods based on monitoring the riveting process, the method proposed in GB2425179 is to be applied once the rivet is completely installed, and is intended for analysing riveted attachments of the same material or different materials. Said method is based on analyzing the electrical impedance of the rivet. It consists of measuring the electrical impedance of the rivet to be evaluated by means of using an ultrasonic generator in a narrow bandwidth. Both the real and complex electrical impedance measured are compared with previously established reference thresholds.

The main technical problem which the invention solves is that of finding a technical solution to the contactless evaluation of blind rivets installed in closed structures or structures for which it is complicated or costly to access the "unexposed face", based on the analysis of the riveting step and the subsequent evaluation for immediately classifying the rivet as suitable or unsuitable.

SUMMARY

The present invention solves the problem described above by means of a non-invasive method for evaluating the installation of a blind rivet used in attaching structures according to claim 1, a system for creating a time relation pattern according to claim 10, and an aircraft according to claim 12.

The invention relates to a non-invasive method for evaluating the installation of a blind rivet used in attaching structures, where the blind rivet comprises a stem, an installation nut, a break notch, cut-off points and a bushing, characterised by comprising the steps of:

a) measuring the "cycle time" defined as the installation time of the rivet which is installed and represented as "$y_0$", The installation "cycle time", which is the time elapsing from the start of a riveting operation until the end of the operation, is measured during the installation of a blind rivet. The cycle time is obtained as the time elapsed between an event representing the start of the installation cycle and an event representing the end of the cycle. This time is represented as "$y_0$".

b) transmitting sound waves through the blind rivet installed in the structure,

The sound is a mechanical vibration which is propagated in materials. A generator generates the sound waves and they are transmitted through the installed blind rivet.

c) measuring the "travel time" defined as the propagation time of the transmitted and reflected sound wave, and represented as "$x_0$", Sound waves are only propagated through a material means, therefore when a wave reaches the boundary of the material in which it is being propagated it cannot continue to advance and is reflected. If there is another material in the boundary, part of the wave is propagated in the second material and part is reflected in the first material. The fact that sound is transmitted and reflected allows it to be used to find out some physical properties of the material in which they are propagated. The "travel time" measurement is directly related to the length of the stem of the rivet after its complete installation, including the machining of the stem if the application so requires. This time is represented as "$x_0$".

The receiver receives the sound waves which are reflected at the end of the travel through the installed blind rivet. The total time from the transmission of the wave through the installed blind rivet and the reception of the reflected sound wave is called "travel time".

d) relating the "travel time" and the "cycle time", and obtaining a pair of times ($x_0,y_0$), The comparison of the "travel time" and "cycle time" magnitudes allows drawing up a "travel time—cycle time" plan on which to represent the pair ($x_0,y_0$).

e) providing a time relation pattern establishing a borderline, or border, in a graphic representation the coordinates of which are (travel time, cycle time) or (x, y), between an area of suitable rivets and an area of unsuitable rivets, where the border is represented as y=f(x), such that
for cycle time values greater than y=f(x), it is considered a "suitable area",
for cycle time values less than y=f(x), it is considered an "unsuitable area";

A characterising pattern of installation "cycle time" and "travel time" is provided in this step. The pattern is a border separating two areas in a graph of coordinates (x, y). An area, the "suitable area", corresponds to pairs (x, y) for rivets the installations of which are "suitable", and the other area, "the unsuitable area", corresponds to pairs (x, y) of rivets the installations of which are "unsuitable".

f) representing the pair ($x_0,y_0$) in the graphic representation and verifying if the value of $y_0$ is greater or less than the value of y=f(x0), The time relation value of the installed rivet ($x_0,y_0$) is compared with the time relation pattern in this step, obtaining a position in the plan in which to represent the installation performed. Depending on the position of ($x_0,y_0$), there will be a point located above or below the border y=f(x), these areas corresponding with the "suitable area" and the "unsuitable area".

g) classifying the installation of the rivet as suitable or unsuitable according to the verification, such that
if $y_0>f(x_0)$ then it is considered a suitable installation
if $y_0<f(x_0)$ then it is considered an unsuitable installation;

Depending on the position in the plan where the performed installation (x0, y0) is represented, the installation is immediately classified as suitable or unsuitable. In other words, if the representation of the installation is located in the area of the "suitable area" plan (x, y), the installation is considered "suitable", and if it is located outside this area, the installation is considered "unsuitable".

As can be seen, the method of the invention is an alternative method to the state of the art, with a different approach, which is based on analysing the riveting step (during the process) and analysing information of the end result (after riveting). The contrast of the information obtained with a pattern according to the method proposed in the present invention is an instant and reliable tool for classifying blind rivets.

In a second inventive aspect, a system is presented for installing blind rivets in structures implementing the method described above and comprising a riveting machine with means for measuring the "cycle time" and a sound wave transmitter with means for injecting said sound waves in an installed rivet and means for measuring the "travel time".

In a third inventive aspect, a method is presented for creating a time relation pattern relating "cycle time" with "travel time", characterised in that it comprises the steps of:
providing a set of rivets to install and a structure in which it is possible to verify the quality of the installed rivet,
installing each rivet in the structure and measuring for each one the "cycle time" represented as $y_p$, with p=A . . . B, where $y_A$ is the minimum "cycle time" that can be implemented for installing a rivet, and $y_B$ is the maximum "cycle time" that can be implemented, This time the cycle time to create the pattern is represented as $y_p$. In the installation of rivets, it is necessary that at least one time is used to install them.

This time is represented as $y_A$ and defines the minimum time necessary to install a blind rivet. It is likewise physically necessary for there to be a maximum cycle or installation time and this time is represented as $y_B$.

once each rivet is installed, measuring the "travel time" and representing it as $x_p$, with p=A . . . B, where $x_A$ is the minimum "travel time" that can be implemented for installing a rivet, and $x_B$ is the maximum "travel time" that can be implemented;

The travel time to create the pattern is represented as $x_p$. In installed rivets, it is physically necessary for this time to be greater than a minimum represented as $x_A$ and it defines the minimum travel time of a sound wave and its reflection through the installed blind rivet. Given the finite length of the installed rivet, there is a maximum length for which a maximum travel time, $x_B$, is associated.

verifying the quality of the installation of each rivet,
representing "travel time" and "cycle time" for each installation of each rivet in a graph with coordinates (x, y) and marking each installation as "suitable" or "unsuitable" according to the quality of the installation of each rivet,
plotting a border y=f(x), $x \in [x_A, x_B]$, and $\in [y_A, y_B]$ representing values of "$y_p=f(x_p)$" above which the installations are considered "suitable" and below which the installations are considered "unsuitable", therefore, there are two areas, "suitable area" and "unsuitable area", separated by the border y=f(x).

For the graphic representation of the times of the installed rivet, the $x_p$, $y_p$ values thereof are considered and are represented in a graph of coordinates (x, y). According to the quality of the installed rivet which has been evaluated since it has been installed in a structure in which accessing the "unexposed" face is possible, it is marked as "suitable installation" or "unsuitable installation". The quality level of each installation is determined depending on the user implementing the method. Once the cycle and travel times of the rivets of the set have been represented, those rivets the installations of which are "suitable" are grouped in a region called "suitable area" and the rivets the installations of which are "unsuitable" are grouped in a region called "unsuitable area". These regions are divided by a border. Dividing the plan in regions, as well as the quality level associated with each region, is performed depending on a user and the quality requirements considered by the user. The regions can be determined as regions in which the quality level of the installation of the contained rivets is predominantly the same. There can even be regions of uncertainty, for example the borders, in which there is no associated quality level, and the rivets in said areas do not have associated quality level.

In a fourth inventive aspect, a system is presented for creating a time relation pattern characterised in that it comprises:
- a set of blind rivets,
- a structure in which it is possible to verify the quality of an installed rivet,
- a system for installing blind rivets according to the second inventive aspect,
- means of viewing the quality of an installed rivet,
- processing means comprising data capture means suitable for receiving and relating "cycle time" and "travel time" of each installation of each rivet and for marking each installation as "suitable" or "unsuitable" according to the quality of the installation of each rivet,
- processing means suitable for generating a "cycle time"=f ("travel time") relation determining a "suitable area" comprising the "suitable" installations in a graphic representation of "cycle time"-"travel time" and an "unsuitable area",
- output means for providing the result, this result being the "cycle time"=f("travel time") relation, and characterised in that it implements the steps of a method according to the third inventive aspect.

In a fifth inventive aspect, a system is presented for installing and evaluating blind rivets comprising
- a system for installation according to the second inventive aspect,
- a system providing a pattern according to the fourth inventive aspect,
- means of viewing the result of the quality of an installed blind rivet, this quality being "suitable" or "unsuitable", and characterised in that it implements the steps of a method according to the first inventive aspect.

Lastly, in a sixth inventive aspect, an aircraft is presented comprising at least one rivet installed by a system for installing and evaluating blind rivets like that of the fifth inventive aspect.

All the technical features described in this specification (including the claims, description and drawings) can be changed in any combination, except the combinations of such mutually excluding features.

DETAILED DESCRIPTION

These and other features and advantages of the invention will become more evident from the following detailed description of preferred embodiments, given only by way of illustrative and non-limiting example, in reference to the attached figures.

FIG. 1 shows a pull-through blind rivet with a countersunk head.

FIG. 2 shows an installed pull-through blind rivet with a countersunk head.

FIG. 3 shows a sound wave transmitter on the countersunk head of a rivet.

DETAILED DESCRIPTION

Figure 5:
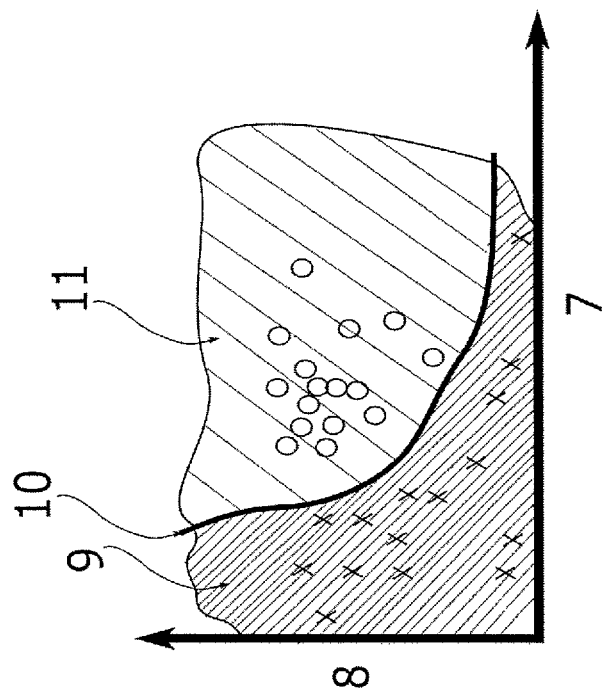
FIG. 5 shows the division of the "travel time—cycle time" plan by the border determining the area of suitable and unsuitable installations.

The present invention relates to a method for evaluating the installation of a blind rivet used in attaching closed structures or structures for which it is complicated or costly to access the "unexposed face" for verifying whether or not the rivets have been correctly installed. An example of a blind rivet is depicted in FIG. 1. A pull-through blind rivet with a countersunk head can be seen in this figure. It shows the different parts of a rivet: stem (1), installation nut (2), break notch (3), cut-off points (4) and bushing (5). FIG. 2 shows the rivet of FIG. 1 installed in a structure where the bushing (5) is folded and can be seen abutting with the structure to prevent the rivet from coming out. The length of the rivet is represented as less than in FIG. 1 due to the breaking of the stem (1).

Non-Invasive Method for Evaluating the Installation of a Rivet

In one embodiment, the non-invasive method for evaluating the installation of a blind rivet used in attaching structures, where the blind rivet comprises a stem (1), an installation nut (2), a break notch (3), cut-off points (4) and a bushing (5), comprises the steps of:
a) measuring the "cycle time" (8) defined as the installation time of the rivet which is installed and represented as "$y_0$",
b) transmitting sound waves through the blind rivet installed in the structure,
c) measuring the "travel time" (7) defined as the propagation time of the transmitted and reflected sound wave, and represented as "$x_0$",
d) relating the "travel time" and the "cycle time", and obtaining a pair of times ($x_0, y_0$),
e) providing a time relation pattern establishing a borderline in a graphic representation the coordinates of which are (travel time, cycle time) or (x, y) between an area of suitable rivets and an area of unsuitable rivets, where the border is represented as y=f(x), such that
   for cycle time values greater than y=f(x), it is considered a "suitable area",
   for cycle time values less than y=f(x), it is considered an "unsuitable area",
f) representing the pair ($x_0, y_0$) in the graphic representation and verifying if the value of $y_0$ is greater or less than the value of y=f(x0),
g) classifying the installation of the rivet as suitable or unsuitable according to the verification, such that
   if $y_0 > f(x_0)$ then it is considered a suitable installation
   if $y_0 < f(x_0)$ then it is considered an unsuitable installation.

In one embodiment, the sound waves transmitted in step b) of the method for evaluating the installation of the rivet are ultrasounds, i.e., frequency thereof exceeds 20 KHz. This feature provides the method with discretion since the human ear is not capable of perceiving sounds at this frequency. In a particular embodiment, the frequency of the sound waves used is 20 MHz.

For measuring the "travel time" correctly a suitable frequency must be used, and to that end the precision of such measurement is greater with high frequencies. However, the attenuation of the sound wave is greater when the frequency is high, and in turn, if the frequency is too high the wave can completely attenuate and it would not be possible to measure the travel time. Therefore, a compromise between precision and attenuation is necessary. Ultrasound waves in the 20 MHz frequency are advantageously used, thereby measuring the "travel time" with sufficient precision.

System for Installing Blind Rivets

In one embodiment, the system for installing blind rivets comprises:
- a riveting machine with means for measuring the "cycle time" of the installation, and
- a sound wave transmitter (6) comprising:
  - means for transmitting sound waves,
  - means of injecting the waves into a rivet and
  - means for measuring the "travel time".

In one embodiment of the system, ultrasound waves at 20 MHz are used and a 20 MHz ultrasound wave generator-transmitter (6) is used. As can be seen in FIG. 3, the same sound wave generator-transmitter (6) is used as emitter-transmitter and receiver generating ultrasound waves and receiving the reflected waves, placing it on the installed rivet for injecting the ultrasound wave at 20 MHz into the rivet and thus being able to measure the "travel time".

In one embodiment of the system, the machine which installs the rivet incorporates a numerical control suitable for measuring the "cycle time".

Method for Creating a Time Relation Pattern

In one embodiment, the method for creating a time relation pattern relating "cycle time" with "travel time" comprises the steps of:
- providing a set of rivets to install and a structure in which it is possible to verify the quality of the installed rivet,
- installing each rivet in the structure and measuring for each one the "cycle time" represented as $y_p$, with p=A . . . B, where $y_A$ is the minimum "cycle time" that can be implemented for installing a rivet, and $y_B$ is the maximum "cycle time" that can be implemented,
- once each rivet is installed, measuring the "travel time" and representing it as $x_p$, with p=A . . . B, where $x_A$ is the minimum "travel time" that can be implemented for installing a rivet, and $x_B$ is the maximum "travel time" that can be implemented,
- verifying the quality of the installation of each rivet,
- representing "travel time" and "cycle time" for each installation of each rivet in a graph with coordinates (x, y) and marking each installation as "suitable" or "unsuitable" according to the quality of the installation of each rivet,
- plotting a border y=f(x), x ∈ [$x_A$, $x_B$], and ∈ [$y_A$, $y_D$], representing values of "$y_p$=f($x_p$)" above which the installations are considered "suitable" and below which the installations are considered "unsuitable", therefore, there are two areas, "suitable area" and "unsuitable area", separated by the border y=f(x).

The method for creating a pattern generates a graphic representation of "suitable" and "unsuitable" installations based on the "travel time" and the "cycle time" as well as a border y=f(x) determining two regions: "suitable area" and "unsuitable area".

Figure 4:
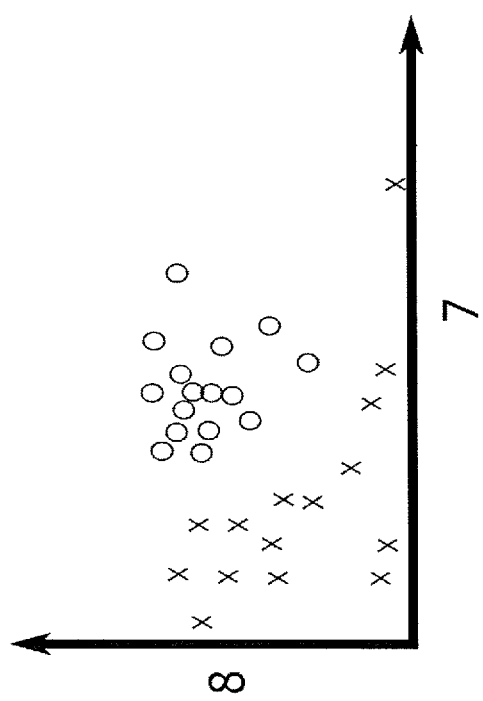
FIG. 4 shows an example of the characterisation result of the "travel time—cycle time" plan.

FIG. 4 is an example of the characterisation result of the "travel time" (7)—"cycle time" (8) plan as a result of a group of rivets used to create the pattern. The group of rivets is installed in a structure in which accessing the "unexposed" face is possible to evaluate the quality. For each indicated rivet, its "travel time" (7) and its "cycle time" (8) is obtained, and the "unexposed face" is accessed to evaluate the quality of the installation of the rivet. A technician decides which quality level is acceptable inspecting the installed rivets and represents the rivets in the plan of FIG. 4, circles (O) correspond to the positions in the "travel time" (7)—"cycle time" (8) plan of rivets the quality of which is considered "suitable", and exes (X) correspond to the positions in the plan of rivets the quality of which is considered "unsuitable".

FIG. 5 shows the division of the "travel time" (7)—"cycle time" (8) plan depending on the two regions defined by the suitable and the unsuitable rivets. The two regions are referred to as "suitable area" (11) and "unsuitable area" (9) and are separated by the border (10). The border corresponds to the relation y=f(x) and represents values of "$y_p$=f($x_p$)" above which the installations are considered "suitable" and below which the installations are considered "unsuitable", therefore, there are two areas, "suitable area" and "unsuitable area", separated by the border y=f(x).

Figure 6:
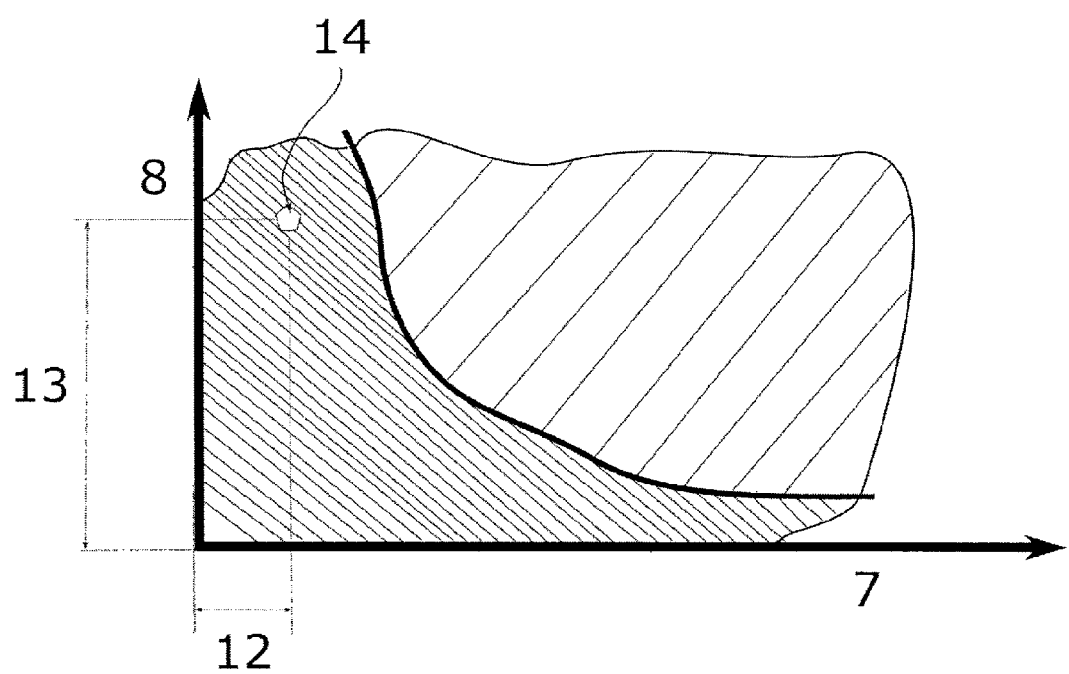
FIG. 6 shows the "travel time—cycle time" plan already characterised, and the method for evaluating a rivet to be evaluated.

FIG. 6 shows the "travel time" (7)—"cycle time" (8) plan of an already installed rivet, and the method for evaluating the rivet to be evaluated (14). Given the "travel time of the rivet to be evaluated" (12), or $x_0$, and the "cycle time of the rivet to be evaluated" (13), or $y_0$, the position (14) of the rivet to be evaluated corresponds to the "unsuitable area" (9) since it is seen that y=f(x0)>y0, and the installation of the rivet is therefore classified as "unsuitable".

Figure 7:
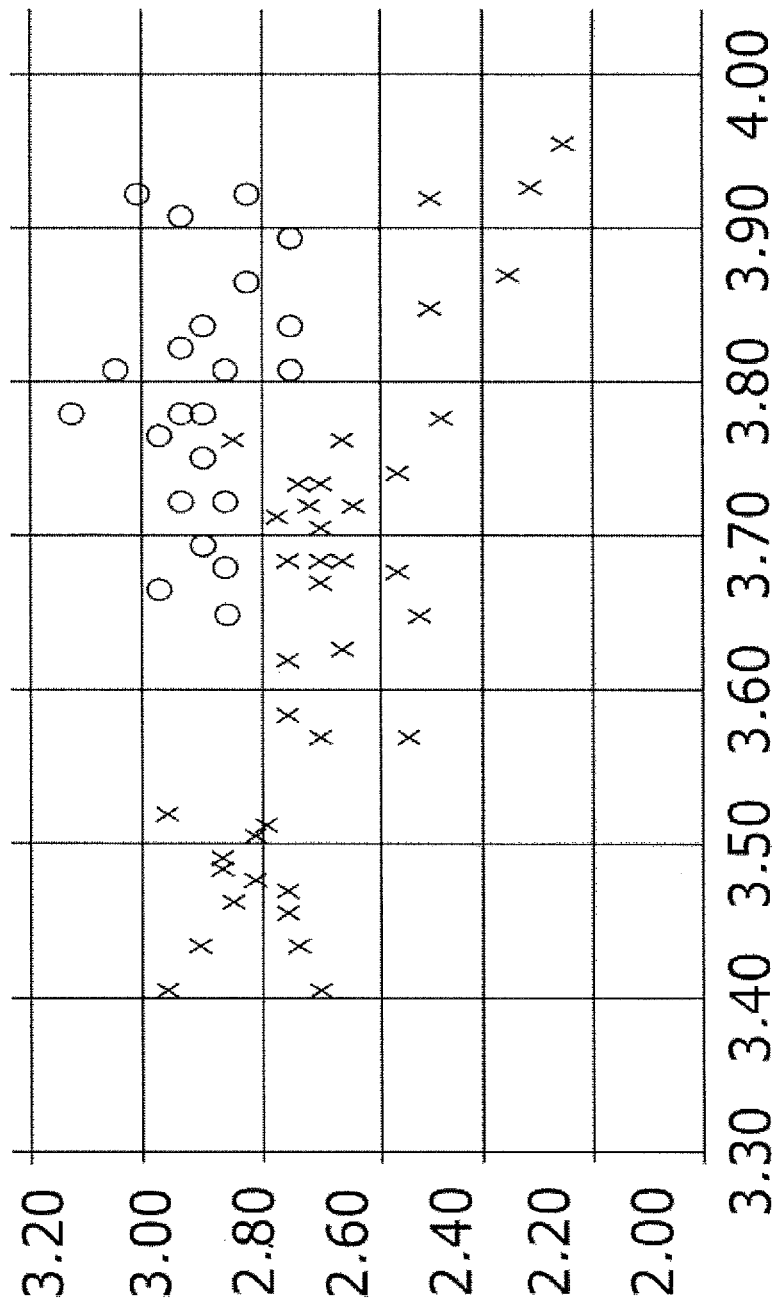
FIG. 7 shows a graph of a first actual experiment where the cycle time is represented on the y-axis in seconds and the travel time on the x-axis in microseconds.

FIG. 7 shows the results of a first experiment with real time values used in the installation of each represented rivet. Circles (O) represent suitable rivets and exes (X) represent rivets which are considered unsuitable. In the graph, the x-axis represents "travel time" in microseconds (µs) and the y-axis represents "cycle time" in seconds (s). Some of the values of the following table (Table 1) are represented in the graph of FIG. 7. "M" represents unsuitable installations and "B" represents suitable installations:

TABLE 1

| Installation | Travel time (µs) | Cycle time (s) |
|---|---|---|
| M | 3.92 | 2.76 |
| M | 3.98 | 2.61 |
| M | 3.95 | 2.82 |
| M | 3.92 | 2.72 |
| M | 3.96 | 2.84 |
| M | 3.92 | 2.73 |
| M | 3.81 | 2.99 |
| M | 3.93 | 2.66 |
| M | 3.98 | 2.87 |
| M | 3.92 | 2.67 |
| M | 3.91 | 2.81 |
| M | 3.86 | 2.86 |
| M | 3.94 | 2.99 |
| M | 4.08 | 2.57 |
| M | 3.94 | 2.73 |
| M | 3.94 | 2.78 |
| M | 3.85 | 2.84 |
| B | 4.37 | 2.94 |
| B | 4.29 | 2.82 |
| B | 4.34 | 2.76 |
| B | 4.33 | 2.80 |
| B | 4.31 | 2.70 |
| B | 4.35 | 2.79 |
| B | 4.43 | 2.85 |
| B | 4.36 | 2.75 |
| B | 0.03 | 1.27 |
| B | 4.30 | 2.89 |
| B | 4.33 | 2.80 |
| B | 4.33 | 2.77 |
| B | 4.43 | 2.92 |
| B | 4.42 | 2.84 |
| B | 4.40 | 3.01 |

TABLE 1-continued

| Installation | Travel time (μs) | Cycle time (s) |
|---|---|---|
| B | 4.32 | 2.93 |
| B | 4.28 | 2.87 |
| B | 4.39 | 2.80 |
| M | 3.90 | 2.87 |
| M | 3.94 | 2.77 |
| M | 3.96 | 2.68 |
| M | 3.92 | 2.73 |
| M | 3.91 | 2.80 |
| M | 3.87 | 2.73 |
| M | 4.38 | 2.24 |
| M | 3.97 | 2.60 |
| M | 3.95 | 2.67 |
| B | 4.32 | 2.83 |
| B | 4.31 | 2.80 |
| M | 3.98 | 2.68 |
| M | 3.92 | 2.83 |
| M | 3.90 | 2.71 |
| M | 3.90 | 2.68 |
| M | 3.95 | 2.66 |
| B | 4.41 | 2.98 |
| B | 4.30 | 3.06 |
| B | 4.47 | 2.92 |
| B | 4.30 | 2.94 |
| B | 4.27 | 2.85 |
| B | 4.32 | 2.88 |
| B | 4.32 | 2.92 |
| B | 4.40 | 2.92 |
| B | 4.29 | 2.90 |
| B | 4.24 | 2.98 |
| B | 4.36 | 2.91 |
| B | 4.36 | 2.70 |

Figure 8:
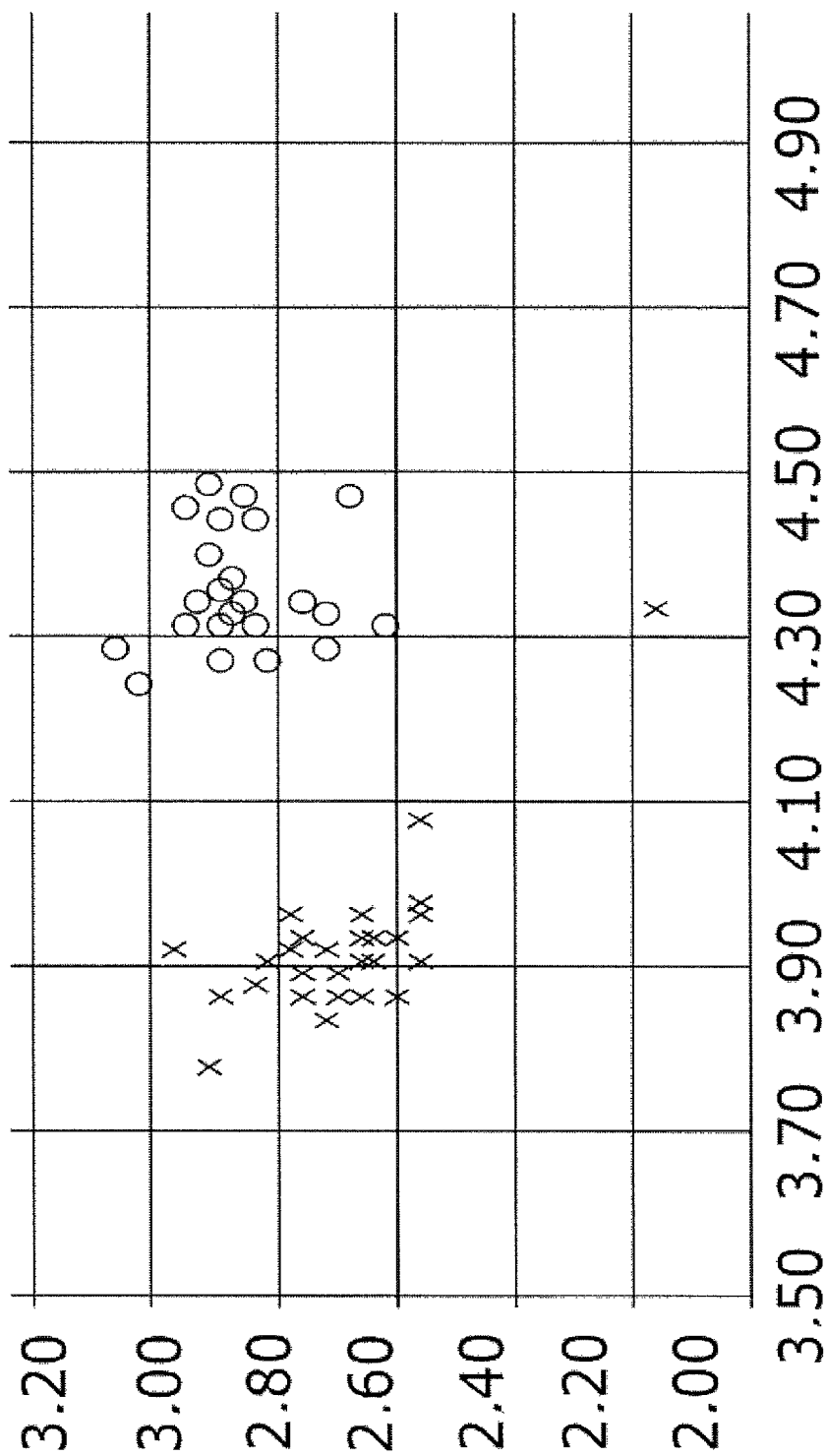
FIG. 8 shows a graph of a second actual experiment where the cycle time is represented on the y-axis in seconds and the travel time on the x-axis in microseconds.

FIG. 8 shows the results of a second experiment with real time values used in the installation of each represented rivet. Circles (O) represent suitable rivets and exes (X) represent rivets which are considered unsuitable. In the graph, the x-axis represents the "travel time" in microseconds (μs) and the y-axis represents "cycle time" in seconds (s). Some of the values of the following table (Table 2) are represented in the graph of FIG. 8. "M" represents unsuitable installations and "B" represents suitable installations:

TABLE 2

| Installation | Travel time (μs) | Cycle time (s) |
|---|---|---|
| M | 3.49 | 2.86 |
| M | 3.53 | 2.97 |
| M | 3.48 | 2.86 |
| B | 3.91 | 3.01 |
| B | 3.79 | 3.23 |
| B | 3.82 | 2.96 |
| M | 3.64 | 2.79 |
| M | 3.68 | 2.62 |
| M | 3.79 | 2.50 |
| M | 3.90 | 2.50 |
| M | 3.67 | 2.74 |
| M | 3.59 | 2.75 |
| M | 3.63 | 2.74 |
| M | 3.67 | 2.73 |
| M | 3.88 | 2.52 |
| M | 3.52 | 2.79 |
| M | 3.69 | 2.74 |
| B | 3.90 | 2.93 |
| B | 3.76 | 3.31 |
| B | 3.81 | 2.87 |
| B | 3.77 | 2.94 |
| B | 3.81 | 2.85 |
| B | 3.72 | 2.99 |
| B | 3.88 | 2.88 |
| B | 3.77 | 3.02 |
| B | 3.80 | 2.83 |
| B | 3.84 | 2.84 |
| B | 3.89 | 2.75 |
| M | 3.64 | 2.74 |

TABLE 2-continued

| Installation | Travel time (μs) | Cycle time (s) |
|---|---|---|
| M | 3.75 | 2.82 |
| M | 3.75 | 2.54 |
| M | 3.71 | 2.72 |
| M | 3.80 | 2.46 |
| M | 3.91 | 2.41 |
| M | 3.67 | 2.71 |
| M | 3.80 | 2.51 |
| M | 3.72 | 2.79 |
| M | 3.41 | 3.00 |
| M | 3.64 | 2.77 |
| M | 3.45 | 2.70 |
| M | 3.65 | 2.71 |
| M | 3.92 | 2.35 |
| M | 3.81 | 2.63 |
| M | 3.42 | 2.74 |
| M | 3.42 | 2.93 |
| M | 3.40 | 2.75 |
| M | 3.45 | 2.86 |
| M | 3.47 | 2.69 |
| M | 3.45 | 2.70 |
| B | 3.75 | 3.00 |
| B | 3.71 | 3.05 |
| B | 3.76 | 2.92 |
| B | 3.67 | 3.03 |
| B | 3.74 | 3.02 |
| B | 3.66 | 3.15 |
| B | 3.82 | 2.82 |
| B | 3.74 | 3.12 |
| B | 3.69 | 3.09 |
| B | 3.75 | 3.06 |
| B | 3.74 | 2.93 |
| B | 3.64 | 3.07 |
| B | 3.73 | 3.04 |
| B | 3.86 | 3.05 |

In one embodiment of the method, the "cycle time" is defined as the time elapsed between the opening of pneumatic valves of the machine used to perform the riveting and the instant the stem (1) of the rivet breaks. This data is obtained by means of external sensors or other similar means.

In one embodiment of the method, the "cycle time" is provided by a numerical control which the machine installing the rivet incorporates.

In one embodiment of the method for creating a time relation pattern, the "travel time" is measured by the pulse-echo method where the receiver is the same sound wave generator.

System for Creating a Time Relation Pattern

In one embodiment, the system for creating a time relation pattern comprises:
  a set of blind rivets,
  a structure in which it is possible to verify the quality of an installed rivet,
  a system for installing blind rivets according to the second inventive aspect or any of the embodiments thereof described above,
  means of viewing the quality of an installed rivet,
  processing means comprising data capture means suitable for receiving and representing "cycle time" and "travel time" of each installation of each rivet in a graph and for marking each installation as "suitable" or "unsuitable" according to the quality of the installation of each rivet,
  processing means suitable for generating a "cycle time"=f ("travel time") relation determining a "suitable area" comprising the "suitable" installations in a graphic representation of "cycle time"-"travel time" and an "unsuitable area", output means for providing the result, this result being the "cycle time"=f("travel time") relation, wherein the system for creating a time relation pattern it implements the steps of the non-invasive method for evaluating the installation of a blind rivet according to the first inventive aspect or any of the embodiments thereof described above.

System for Installing and Evaluating Blind Rivets

In one embodiment, the system for installing and evaluating blind rivets comprises
- a system for installing blind rivets according to the first inventive aspect or any of the embodiments thereof described above,
- a system for creating a pattern according to the fourth inventive aspect or any of the embodiments thereof described above,
- means of viewing the result of the quality of a blind rivet, this quality being "suitable" or "unsuitable", wherein the system implements the steps of a method according to the first inventive aspect or any of the embodiments thereof described above.

The invention claimed is:

1. A non-invasive method for evaluating an installed blind rivet used in attaching structures, where the installed blind rivet comprises a stem, an installation nut, a break notch, cut-off points and a bushing, wherein the method comprises:
   a) measuring "cycle time" defined as installation time of the rivet which is installed and represented as "$y_0$";
   b) transmitting sound waves through the blind rivet installed in the structure;
   c) measuring "travel time" defined as propagation time of transmitted and reflected sound waves of the installed blind rivet, and represented as "$x_0$";
   d) relating the "travel time" and the "cycle time", and obtaining a pair of times ($x_0, y_0$);
   e) providing a time relation pattern establishing a border in a graphic representation the coordinates of which are (travel time, cycle time) or (x, y) between an area of suitable rivets and an area of unsuitable rivets, where the border is represented as y=f(x), such that
      for cycle time values greater than y=f(x), it is considered a "suitable area",
      for cycle time values less than y=f(x), it is considered an "unsuitable area";
   f) representing the pair ($x_0, y_0$) in the graphic representation and verifying if the value of $y_0$ is greater or less than the value of y=f($x_0$); and
   g) classifying the installation of the rivet as suitable or unsuitable according to the verification, such that
      if $y_0 > f(x_0)$ then it is considered a suitable installation
      if $y_0 < f(x_0)$ then it is considered an unsuitable installation.

2. The method according to claim 1, wherein the sound waves are ultrasounds.

3. The method according to claim 2, wherein the frequency of the sound waves is 20 MHZ.

4. The method according to claim 1, where the "cycle time" is obtained as the time elapsed between the opening of pneumatic valves of a machine used to install the rivet and an instant a stem of the rivet breaks.

5. The method according to claim 1, where the "cycle time" is provided by a numerical control of a machine used to install the rivet.

6. The method according to claim 1, wherein the "travel time" is measured by a pulse-echo method in which a receiver is the same generator-transmitter generating and transmitting the sound waves.

7. A system for creating a time relation pattern, wherein the system comprises:
   a set of blind rivets;
   a structure in which to verify quality of an installed rivet;
   a system for installing blind rivets comprising:
      a riveting machine for measuring installation "cycle time", defined as installation time of the rivet which is installed;
      a transmitter which transmits sound waves into installed rivets and measures "travel time", defined as propagation time of transmitted and reflected sounds waves in the installed rivet;
   a device for viewing quality of an installed rivet;
   a process or configured for data capture suitable for receiving and representing "cycle time" and "travel time" of each installation of each rivet in a graph and for marking each installation as "suitable" or "unsuitable" according to the quality of the installation of each rivet;
   wherein the processor is further configured to generate a "cycle time"=f("travel time") relation which defines a border in the graph between "suitable" installations of the installed rivets and "unsuitable" installations of the installed rivets; and
   an output for providing result, this result being the "cycle time"=f("travel time") relation.

8. The system of claim 7, further comprising a non-transitory computer readable medium containing instructions thereon which cause the processor to:
   generate a first data set of two-dimensional points which contains "cycle time", represented as "$y_0$", and measured "travel time", represented as "$x_0$", for each one of a second set of installed rivets; and
   analyze the first data set using the "cycle time"=f("travel time") relation, represented as y=f(x), wherein the analysis comprises:
   for each measured cycle time of each of the second set of installed rivets, classifying a rivet installation as "suitable" if the cycle time value is greater than y=f(x) and "unsuitable" if the cycle time value is less than y=f(x).

9. An aircraft comprising at least one structure installed by a system according to claim 8.

10. The system according to claim 7, wherein the sound waves are ultrasound waves at 20 MHz.

11. The system according to claim 8, wherein the sound waves are ultrasound waves at 20 MHz.

12. An aircraft comprising at least one structure installed by a system according to claim 10.

13. An aircraft comprising at least one structure Installed by a system according to claim11.

* * * * *